United States Patent
Klein

Patent Number: 5,950,238
Date of Patent: Sep. 14, 1999

[54] POST-LIPOSUCTION BREAST COMPRESSION GARMENT AND METHOD FOR EDEMA REDUCTION

[76] Inventor: Jeffrey A. Klein, 30280 Rancho Viejo Rd., San Juan Capistrano, Calif. 92675

[21] Appl. No.: 09/015,731
[22] Filed: Jan. 29, 1998
[51] Int. Cl.⁶ ........................................... A41B 1/00
[52] U.S. Cl. .................... 2/69; 2/114; 604/345; 450/31; 602/13; 128/374
[58] Field of Search ........................ 2/69, 104, 105, 2/106, 113–115, 108, 85, 93, 83, 69.5, 44, 45; 604/345; 602/79, 53, 61, 4, 13, 62, 63, 14, 75, 60; 128/374, 384, 385, 403, 482, 402, 874, 846, 845, DIG. 25; 450/1, 30–32, 58, 79, 80, 91, 85, 54, 55, 70; 606/20

[56] References Cited

U.S. PATENT DOCUMENTS

| | | |
|---|---|---|
| 808,433 | 12/1905 | Cartledge . |
| 3,279,465 | 10/1966 | Cherio et al. . |
| 3,529,601 | 9/1970 | Kirkland . |
| 3,824,996 | 7/1974 | Carlisle . |
| 3,968,803 | 7/1976 | Hyman . |
| 4,215,687 | 8/1980 | Shaw . |
| 4,325,378 | 4/1982 | Wilkinson ........................ 450/1 |
| 4,400,832 | 8/1983 | Kinder . |
| 4,444,191 | 4/1984 | Harned ........................... 450/1 |
| 4,665,909 | 5/1987 | Trainor . |
| 4,829,987 | 5/1989 | Stewart . |
| 4,835,795 | 6/1989 | Lonon . |
| 5,054,129 | 10/1991 | Baehr ............................ 2/409 |
| 5,060,315 | 10/1991 | Ewing ............................ 2/69 |
| 5,109,546 | 5/1992 | Dicker . |
| 5,152,741 | 10/1992 | Farnio .......................... 602/61 |
| 5,171,211 | 12/1992 | Deasy, Jr. ...................... 602/61 |
| 5,257,956 | 11/1993 | Ewen ............................ 450/1 |
| 5,267,352 | 12/1993 | Rodarmel ....................... 2/44 |
| 5,274,851 | 1/1994 | Simpkins, Sr. et al. ............ 2/44 |
| 5,367,708 | 11/1994 | Fujimoto ........................ 2/22 |
| 5,427,563 | 6/1995 | Manning ........................ 450/79 |
| 5,429,593 | 7/1995 | Matory ......................... 602/79 |
| 5,527,270 | 6/1996 | Chase et al. ................... 602/61 |
| 5,582,583 | 12/1996 | Ballantyne ..................... 602/5 |
| 5,603,116 | 2/1997 | Tronc .......................... 2/2.15 |

FOREIGN PATENT DOCUMENTS

| | | |
|---|---|---|
| 2519865 | 7/1983 | France . |

*Primary Examiner*—Gloria Hale
*Attorney, Agent, or Firm*—Stetina Brunda Garred & Brucker

[57] ABSTRACT

A two-component post-operative compression garment for use in enhancing fluid drainage from a plurality of open micro-incisions in breasts after liposuction surgery has been performed on the breasts. The compression garment includes a first garment component positionable on a person to cause a first magnitude of compression pressure upon the breasts, and a second garment component adjustably positionable in concert with the first garment component to cause an adjustable second magnitude of compression pressure greater than the first magnitude. This second magnitude of pressure is adjustable to thereby provide a pressure adequate to force fluid from the open micro-incisions of the breasts. Methodology of liposuction mammoplasty includes infiltrating each breast tumescently with a fluid that includes a local anesthetic. Thereafter, a plurality of micro-incisions are provided to the breasts and fatty tissue is withdrawn suctionally with operating microcannulas inserted within the micro-incisions. Finally, the microcannulas are removed from the open micro-incisions and compression pressure is applied as with the above described compression garment to each breast for a period of time and of a sufficient pressure to force the tumescent fluid from the breasts through the micro-incisions. Substantially identical liposuction methodology can be employed for abdominal areas.

42 Claims, 1 Drawing Sheet

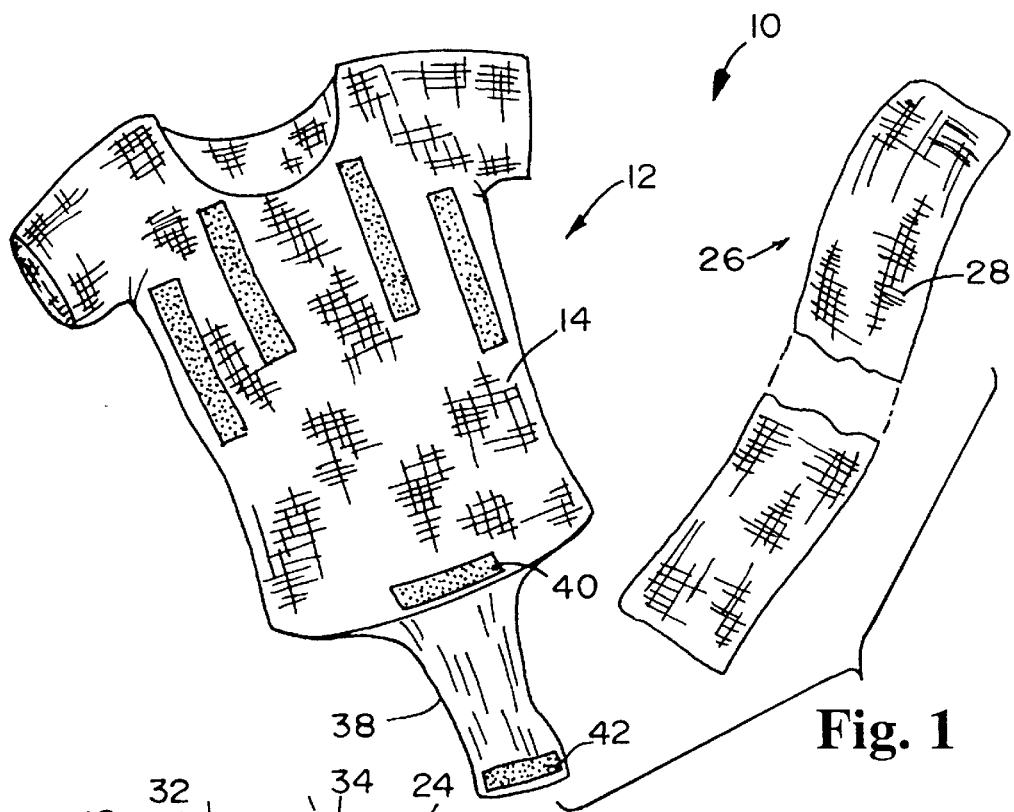
Fig. 1
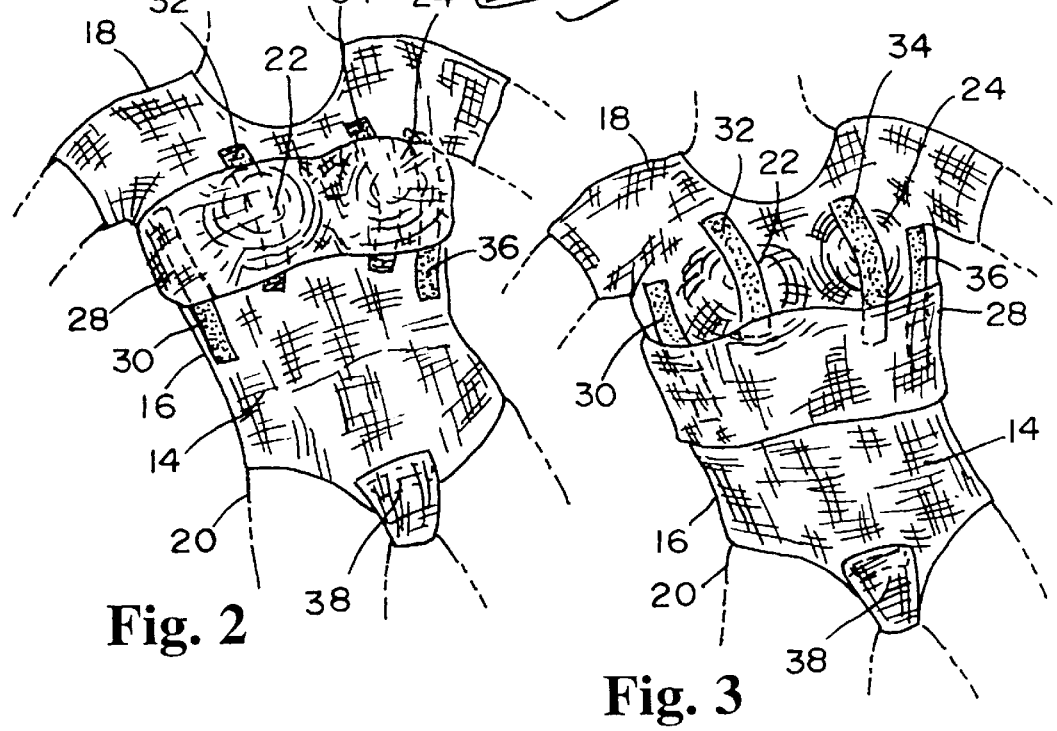
Fig. 2
Fig. 3

POST-LIPOSUCTION BREAST COMPRESSION GARMENT AND METHOD FOR EDEMA REDUCTION

FIELD OF THE INVENTION

This invention relates in general to reduction mammoplasty, and in particular to breast liposuction methodology and a breast compression garment for reducing post-liposuction edema.

BACKGROUND OF THE INVENTION

The traditional solution for achieving breast size reduction in women has been surgical breast reduction by excision. Such reduction is usually sought in order to improve chronic changes in posture as well as degenerative changes and pain in the neck, shoulder and back, and to permit normal participation in athletic and other physical activities. However, excisional breast reduction surgery can have undesirable cosmetic results including breast scarring and asymmetry, as well as post-operative complications including hematomas, seromas, and fat necrosis with pseudocyst formations. Additionally, because of its excisional approach, such traditional surgery requires general anesthesia, and usually results in prolonged post-operative pain and recovery time.

While liposuction at other body sites is a recognized procedure for removing fat deposits, and while a tumescent procedure as developed by the present inventor is exceptionally effective generally in performing liposuction procedures using only local anesthesia, the employment of a tumescent technique for breast reduction has resulted in severe edema, bruising, subcutaneous bleeding, excessive ecchymosis, and hematomas after liposuction. In view of these highly untoward post-procedure disorders, it is apparent that a need is present for effective tumescent breast reduction liposuction. Accordingly, a primary object of the present invention is to provide liposuction methodology for breast reduction wherein untoward post-operative conditions are minimized.

Another object of the present invention is to provide a post-operative compression garment for use in enhancing fluid drainage from a plurality of open micro-incisions in breasts after liposuction surgery.

Yet another object of the present invention is to provide a two component post-operative compression garment wherein compression pressure upon breasts is adjustable for optimum post-operative care.

These and other objects of the present invention will become apparent throughout the description thereof which now follows.

SUMMARY OF THE INVENTION

The present invention is a two component post-operative compression garment for use in enhancing fluid drainage from a plurality of open micro-incisions in breasts after tumescent liposuction surgery has been performed on the breasts. The compression garment comprises a first garment component positionable on a person to cause a first magnitude of compression pressure upon the breasts, and a second garment component adjustably positionable in concert with the first garment component to cause an adjustable second magnitude of compression pressure upon the breasts greater than the first magnitude. This second magnitude of pressure is adjustable to thereby provide a pressure adequate to force fluid from the open micro-incisions of the breasts and to provide hemostasis.

Methodology of tumescent liposuction mammoplasty includes, first, infiltrating each of the breasts tumescently with a tumescent fluid comprising a local anesthetic. Second, a plurality of generally symmetrically disposed micro-incisions of from about 2 mm to about 5 mm, and preferably 2 mm to 3 mm, in length are provided to each of the breasts. Third, fatty tissue is withdrawn from each of the breasts suctionally with operating microcannulas inserted within the micro-incisions. These microcannulas have a very small inside diameter (preferably between about 1.1 mm and 1.8 mm) and a plurality of lateral openings leading into the respective cannulas. Finally, the microcannulas are removed from the open micro-incisions which are not sutured and compression pressure is applied to each of the breasts for a period of time and of a sufficient pressure to force the tumescent fluid from the breasts through the open micro-incisions and to provide hemostasis. Such final treatment can be achieved through employment of the two component post-operative compression garment as defined and described above. In this manner, breast reduction is accomplished through liposuction methodology while simultaneously minimizing untoward post-operative cosmetic and internal medical conditions. Such methodology is likewise employable for abdominal tumescent liposuction procedures in torso areas generally situated between shoulders and thighs.

BRIEF DESCRIPTION OF THE DRAWINGS

An illustrative and presently preferred embodiment of the invention is shown in the accompanying drawings in which:

FIG. 1 is a perspective view of a two component post-operative compression garment showing each component thereof separately;

FIG. 2 is a perspective view of the compression garment of FIG. 1 on a torso of a female with the second garment component in place on the breasts; and FIG. 3 is a perspective view of the compression garment of FIG. 1 on a torso of a female with the second garment component in place beneath the breasts.

DETAILED DESCRIPTION OF THE PREFERRED EMBODIMENT

Referring to FIGS. 1–3, a two component post-operative compression garment 10 is shown. The compression garment 10 has a first garment component 12 which is a body suit 14 generally encircling an anatomical portion 16 of a wearer between a shoulder area 18 and a thigh area 20. The body suit 14 is elasticized to provide a first magnitude of compression pressure to the wearer including the breasts 22, 24 as illustrated in form in FIGS. 2 and 3. The compression garment 10 additionally has a second garment component 26 which is an elasticized binder 28 releasably and adjustably positionable around the wearer much like a belt to cause and permit adjustable compression pressure upon the breasts 22, 24 as shown in FIG. 2.

The first garment component 12 is provided with at least one attachment member, and here has four attachment members 30, 32, 34, 36 here shown as the hook portions only of standard hook-and-loop connectors (e.g. Velcro™ connectors) for accepting and releasably securely retaining the second garment component 26 whose exterior can be a fluff-type fabric as known in the art that adheres to the attachment members 30, 32, 34, 36. As so desired, of course, the second garment component 26 instead can be provided with the "loop" portions (not shown) for traditional hook-and-loop retention. The attachment members 30, 32, 34, 36 are situated both to prevent slippage of the second garment component 26 from its position over the breasts 22, 24 when the wearer moves, stretches, etc., and to cover the entire breasts 22, 24, including areas that may extend above the armpits. Because the first garment component 12 of the preferred embodiment has sleeves, the second garment component 26 does not come in skin contact with the armpits of the wearer and thereby does not irritate the armpit area. FIG. 3 illustrates placement of the second garment component 26 beneath the breasts 22, 24, with like retention to the first garment component 12. As is shown, the attachment members 30, 32, 34, 36 are positioned on the first garment component 12 such that the second garment component 26 is securable either across or beneath the breasts 22, 24. A crotch piece 38 is conventionally securable in a closed position with cooperating hook and loop portions 40, 42.

A method of performing liposuction surgery on breasts of a person first comprises the infiltration of each breast tumescently with tumescent fluid carrying a local anesthetic to thereby reduce pain felt by a patient. Thereafter, a plurality of generally symmetrically disposed micro-incisions of from about 2 mm to about 5 mm in length are made in each of the breasts. Respective microcannulas are inserted within the micro-incisions and fatty tissue is withdrawn suctionally by the operating microcannulas. These microcannulas have an inside diameter of between about 1.1 mm and 1.8 mm, and have a plurality of laterally disposed openings leading into the respective cannulas for acceptance of the fatty tissue.

After withdrawal of the desired quantity of tissue from the desired site(s), the surgeon removes the microcannulas from the open micro-incisions and initiates post-operative compression pressure to each of the breasts for a period of time and of a sufficient pressure to force the tumescent fluid from the breasts through the open micro-incisions. As noted above, the breast is unique in its compression requirements after a liposuction procedure. While most areas of the body do not require an exceptionally high degree of compression after liposuction, the breasts are an exception and do require a higher magnitude of compression especially for the first 12 to 24 hours following the procedure, and possibly up to about 72 hours, to encourage a maximal degree of hemostasis as well as fluid exit from the micro-incisions. If the compression is too slight, there is risk of subcutaneous bleeding, excessive ecchymosis, or hematoma. Conversely, if the compression is too tight, the patient may experience pain. Adjustability of the second garment component 26 above described by simply modifying the tightness with which it encompasses the wearer permits the surgeon to properly achieve the magnitude of compression pressure to meet the needs of each particular patient. Finally, after adequate drainage has occurred, the second garment component 26 is relocated to reside beneath the breasts as shown in FIG. 3 to provide comfortable support as long as indicated by the patient or physician. In this manner, liposuction reduction mammaplasty can be safely and effectively achieved.

As noted above, the methodology here described for breast liposuction also is effective for abdominal liposuction. In such abdominal liposuction procedures, the first garment component is identical to that used for breast reduction mammaplasty, while the second garment component is modified dimensionally as required for the particular anatomical site.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A two component post-operative compression garment for use in enhancing fluid drainage from a plurality of open micro-incisions in breasts after liposuction surgery on said breasts, the compression garment comprising:
    a) a first substantially completely elasticized garment component positionable on a person to cause a first magnitude of compression pressure upon the breasts; and
    b) a second garment component adjustably positionable in concert with the first garment component to cause an adjustable second magnitude of compression pressure upon the breasts greater than the first magnitude, said second magnitude being an adjustable pressure adequate to force fluid from the open micro-incisions of the breasts.

2. A two component post-operative compression garment as claimed in claim 1 wherein the first garment component is a wearable piece of clothing.

3. A two component post-operative compression garment as claimed in claim 2 wherein the wearable piece of clothing is a body suit generally encircling an anatomical portion of a wearer between a shoulder area and a thigh area.

4. A two component post-operative compression garment as claimed in claim 1 wherein the second garment component is a binder releasably adjustably positionable around the person to cause compression pressure upon the breasts.

5. A two component post-operative compression garment as claimed in claim 4 wherein the binder is positionable outside of the first garment component.

6. A two component post-operative compression garment as claimed in claim 5 wherein the binder is elasticized.

7. A two component post-operative compression garment as claimed in claim 1 wherein the first garment component has at least one attachment member for accepting and releasably retaining the second garment component when said second garment component is positioned around the person to cause adjustable compression pressure upon the breasts.

8. A two component post-operative compression garment as claimed in claim 1 wherein the second garment component is releasably adjustably positionable generally beneath the breasts to support the breasts in concert with the first garment component.

9. A two component post-operative compression garment as claimed in claim 8 wherein the second garment component is releasably adjustably positionable around the person generally beneath the breasts to support the breasts in concert with the first garment component.

10. A two component post-operative compression garment as claimed in claim 9 wherein the first garment component has at least one attachment member for accepting and releasably retaining the second garment component when said second garment component is positioned around the person to support the breasts.

11. A method of reducing post-liposuction edema in breasts of a person subsequent to liposuction surgery on said breasts wherein said surgery produced a plurality of open micro-incisions in the breasts, the method comprising:
    a) positioning on the person a two component post-operative compression garment substantially immediately after surgery to cause compression pressure upon the breasts and enhance fluid drainage from the plurality of open micro-incisions of the breasts, the compression garment comprising:

1) a first garment component positionable and so positioned on a person to cause a first magnitude of compression pressure upon the breasts; and 2) a second garment component adjustably positionable and so positioned in concert with the first garment component to cause an adjustable second magnitude of compression pressure upon the breasts greater than the first magnitude, said second magnitude being an adjustable pressure adequate to force fluid from the open micro-incisions of the breasts; and b) retaining the two component post-operative compression garment in place for a period of time sufficient to force said fluid from said open micro-incisions.

12. A method as claimed in claim 11 wherein the first garment component of the compression garment is a wearable piece of clothing.

13. A method as claimed in claim 12 wherein the first garment component is an elasticized vestment.

14. A method as claimed in claim 14 wherein the vestment is a body suit generally encircling an anatomical portion of a wearer between a shoulder area and a thigh area.

15. A method as claimed in claim 14 wherein the second garment component of the compression garment is a binder releasably adjustably positionable around the person to cause compression pressure upon the breasts.

16. A method as claimed in claim 15 wherein the binder is positionable outside of the first garment component.

17. A method as claimed in claim 16 wherein the binder is elasticized.

18. A method as claimed in claim 11 wherein the first garment component of the compression garment has at least one attachment member for accepting and releasably retaining the second garment component when said second garment component is positioned around the person to cause adjustable compression pressure upon the breasts.

19. A method as claimed in claim 11 wherein the second garment component of the compression garment is releasably adjustably positionable generally beneath the breasts to support the breasts in concert with the first garment component.

20. A method as claimed in claim 19 wherein the second garment component is releasably adjustably positionable around the person generally beneath the breasts to support the breasts in concert with the first garment component.

21. A method as claimed in claim wherein the first garment component has at least one attachment member for accepting and releasably retaining the second garment component when said second garment component is positioned around the person to support the breasts.

22. A method as claimed in claim 11 wherein the second garment component is positioned for a period of time from about 12 to about 72 hours.

23. A method as claimed in claim 17 wherein the second garment component is positioned for a period of time from about 12 to about 72 hours.

24. A method as claimed in claim 20 wherein the second garment component is positioned for a period of time from about 12 to about 72 hours and thereafter positioned around the person generally beneath the breasts to support the breasts in concert with the first garment component during lymphatic capillary absorption of fluid remaining in tissue of the breasts.

25. A method of performing liposuction surgery on breasts of a person, the method comprising:

a) infiltrating each of the breasts tumescently with tumescent fluid comprising a local anesthetic;

b) providing a plurality of generally symmetrically disposed micro incisions of from about 2 mm to about 5 mm in length to each of the breasts;

c) withdrawing supranatant fatty tissue from each of the breasts suctionally with operating microcannulas inserted within the micro-incisions, said microcannulas having an inside diameter between about 1.1 mm and 1.8 mm and a plurality of lateral openings thereto;

d) removing the microcannulas from the open micro-incisions and applying compression pressure to each of the breasts for a period of time and of a sufficient pressure to force the tumescent fluid from the breasts through the open micro-incisions;

e) applying compression pressure to each of the breasts by positioning on the person a two component post-operative compression garment substantially immediately after surgery to cause compression pressure upon the breasts and enhance fluid drainage from the plurality of open micro-incisions of the breasts, the compression garment comprising:

i) a first garment component positionable and so positioned on a person to cause a first magnitude of compression pressure upon the breasts; and ii) a second garment component adjustably positionable and so positioned in concert with the first garment component to cause an adjustable second magnitude of compression pressure upon the breasts greater than the first magnitude, said second magnitude being an adjustable pressure adequate to force fluid from the open micro-incisions of the breasts; and f) retaining the two component post-operative compression garment in place for a period of time sufficient to force said fluid from said open micro-incisions.

26. A method as claimed in claim 25 wherein the first garment component of the compression garment is a wearable piece of clothing.

27. A method as claimed in claim 26 wherein the first garment component is an elasticized vestment.

28. A method as claimed in claim 27 wherein the vestment is a body suit generally encircling an anatomical portion of a wearer between a shoulder area and a thigh area.

29. A method as claimed in claim 28 wherein the second garment component of the compression garment is a binder releasably adjustably positionable around the person to cause compression pressure upon the breasts.

30. A method as claimed in claim 29 wherein the binder is positionable outside of the first garment component.

31. A method as claimed in claim 30 wherein the binder is elasticized.

32. A method as claimed in claim 25 wherein the first garment component of the compression garment has at least one attachment member for accepting and releasably retaining the second garment component when said second garment component is positioned around the person to cause adjustable compression pressure upon the breasts.

33. A method as claimed in claim 25 wherein the second garment component of the compression garment is releasably adjustably positionable generally beneath the breasts to support the breasts in concert with the first garment component.

34. A method as claimed in claim 33 wherein the second garment component is releasably adjustably positionable around the person generally beneath the breasts to support the breasts in concert with the first garment component.

35. A method as claimed in claim 34 wherein the first garment component has at least one attachment member for accepting and releasably retaining the second garment component when said second garment component is positioned around the person to support the breasts.

36. A method as claimed in claim 25 wherein the second garment component is positioned for a period of time from about 12 to about 72 hours.

37. A method as claimed in claim 31 wherein the second garment component is positioned for a period of time from about 12 to about 72 hours.

38. A method as claimed in claim 34 wherein the second garment component is positioned for a period of time from about 12 to about 72 hours and thereafter positioned around the person generally beneath the breasts to support the breasts in concert with the first garment component during lymphatic capillary absorption of fluid remaining in tissue of the breasts.

39. A two component post-operative compression garment for use in enhancing fluid drainage from a plurality of open micro-incisions in breasts after liposuction surgery on said breasts, the compression garment comprising:
  a) a first garment component positionable on a person to cause a first magnitude of compression pressure upon the breasts, said first garment comprising a wearable, elasticized body suit clothing vestment generally encircling an anatomical portion of a wearer between a shoulder area and a thigh area; and
  b) a second garment component adjustably positionable in concert with the first garment component to cause an adjustable second magnitude of compression pressure upon the breasts greater than the first magnitude, said second magnitude being an adjustable pressure adequate to force fluid from the open micro-incisions of the breasts.

40. A two component post-operative compression garment for use in enhancing fluid drainage from a plurality of open micro-incisions in breasts after liposuction surgery on said breasts, the compression garment comprising:
  a) a first garment component positionable on a person to cause a first magnitude of compression pressure upon the breasts; and
  b) a second garment component adjustably positionable in concert with the first garment component to cause an adjustable second magnitude of compression pressure upon the breasts greater than the first magnitude, said second magnitude being an adjustable pressure adequate to force fluid from the open micro-incisions of the breasts, with said first garment component having at least one attachment member for accepting and releasably retaining the second garment component when said second garment component is positioned around the person to cause adjustable compression pressure upon the breasts.

41. A two component post-operative compression garment for use in enhancing fluid drainage from a plurality of open micro-incisions in breasts after liposuction surgery on said breasts, the compression garment comprising:
  a) a first garment component positionable on a person to cause a first magnitude of compression pressure upon the breasts; and
  b) a second garment component adjustably positionable in concert with the first garment component to cause an adjustable second magnitude of compression pressure upon the breasts greater than the first magnitude, said second magnitude being an adjustable pressure adequate to force fluid from the open micro-incisions of the breasts, wherein said second garment component releasably adjustably positionable around the person generally beneath the breasts to support the breasts in concert with the first garment component, and wherein the first garment component has at least one attachment member for accepting and releasably retaining the second garment component when said second garment component is positioned around the person to support the breasts.

42. A two component post-operative compression garment for use in enhancing fluid drainage from a plurality of open micro-incisions in breasts after liposuction surgery on said breasts, the compression garment comprising:
  a) a first garment component positionable on a person to cause a first magnitude of compression pressure upon the breasts; and
  b) a second garment component comprising an elasticized binder positionable outside of the first garment component adjustably positionable in concert with the first garment component to cause an adjustable second magnitude of compression pressure upon the breasts greater than the first magnitude, said second magnitude being an adjustable pressure adequate to cause compression pressure upon the breasts and force fluid from the open micro-incisions of the breasts.

* * * * *